United States Patent
Gojo et al.

(10) Patent No.: US 12,037,573 B2
(45) Date of Patent: Jul. 16, 2024

(54) TUBULAR CELL STRUCTURE CULTIVATION MAINTAINING APPARATUS AND TUBULAR CELL STRUCTURE MAINTAINING SUPPORT DEVICE

(71) Applicant: CYFUSE BIOMEDICAL K.K., Tokyo (JP)

(72) Inventors: Satoshi Gojo, Kyoto (JP); Daisuke Kami, Kyoto (JP); Kumika Matsubayashi, Fukuoka (JP); Shizuka Akieda, Fukuoka (JP)

(73) Assignee: CYFUSE BIOMEDICAL K.K., Tokyo (JP)

( * ) Notice: Subject to any disclaimer, the term of this patent is extended or adjusted under 35 U.S.C. 154(b) by 104 days.

(21) Appl. No.: 17/046,114

(22) PCT Filed: Apr. 9, 2018

(86) PCT No.: PCT/JP2018/014895
§ 371 (c)(1),
(2) Date: Oct. 8, 2020

(87) PCT Pub. No.: WO2019/198126
PCT Pub. Date: Oct. 17, 2019

(65) Prior Publication Data
US 2021/0032585 A1 Feb. 4, 2021

(51) Int. Cl.
*C12M 1/00* (2006.01)
*C12M 1/12* (2006.01)

(52) U.S. Cl.
CPC ............ *C12M 29/04* (2013.01); *C12M 23/06* (2013.01); *C12M 25/10* (2013.01)

(58) Field of Classification Search
None
See application file for complete search history.

(56) References Cited

U.S. PATENT DOCUMENTS 5,490,933 A * 2/1996 LaPack ............... C02F 1/20
210/603
6,537,567 B1 3/2003 Niklason et al.
(Continued)

FOREIGN PATENT DOCUMENTS

DE 10 2005 001 747 A1 7/2006
EP 1 382 670 A1 1/2004
(Continued)

OTHER PUBLICATIONS

Hu et al. "Construction and characterization of anelectrospun tubula rscaffold for small-diamete rtissue-engineered vascular grafts: A scaffold membrane approach", Journal of the Mechanical Behavior of Biomedical Materials, 13(2012) 140-155. (Year: 2012).*
(Continued)

*Primary Examiner* — William H. Beisner
(74) *Attorney, Agent, or Firm* — Birch, Stewart, Kolasch & Birch, LLP (57) ABSTRACT

It is solved by the rod-shaped tubular cell structure maintaining support device for cultivating a tubular cell structure including a hollow portion inside for a predetermined period of time while maintaining the hollow portion, the tubular cell structure maintaining support device including an outer diameter insertable into the hollow portion of the cell structure, and when inserted into the hollow portion, capable of allowing the tubular cell structure maintaining support device to adhere to an inner surface of the cell structure, and a penetration conduit including openings at both ends of the tubular cell structure maintaining support device, and penetrating between the openings, wherein the tubular cell structure maintaining support device has an oxygen permeable structure from the penetration conduit to an outer surface of the tubular cell structure maintaining support device.

6 Claims, 4 Drawing Sheets

(56) References Cited

U.S. PATENT DOCUMENTS

| | | |
|---|---|---|
| 6,921,662 B2 | 7/2005 | Takagi et al. |
| 8,198,086 B2 | 6/2012 | Koga et al. |
| 9,090,863 B2 | 7/2015 | Breuer et al. |
| 2004/0203147 A1 | 10/2004 | Triffitt et al. |
| 2005/0009178 A1 | 1/2005 | Yost et al. |
| 2011/0033927 A1 | 2/2011 | Rolle et al. |
| 2017/0342373 A1 | 11/2017 | Wan et al. |
| 2019/0169558 A1 | 6/2019 | Sankai |
| 2020/0406542 A1* | 12/2020 | Bennett ............... B29C 64/35 |

FOREIGN PATENT DOCUMENTS

| | | | |
|---|---|---|---|
| JP | 2002-315566 A | 10/2002 | |
| JP | 2005-502351 A | 1/2005 | |
| JP | 2006-311887 A | 11/2006 | |
| JP | 4517125 B2 | 8/2010 | |
| JP | 2012-120696 A | 6/2012 | |
| JP | 2013-529081 A | 7/2013 | |
| JP | 2016-77229 A | 5/2016 | |
| JP | 2017-143775 A | 8/2017 | |
| WO | WO-9637165 A1 * | 11/1996 | ............ A61L 27/16 |
| WO | WO-9749799 A1 * | 12/1997 | ............ A61F 2/062 |
| WO | WO 2011/146046 A1 | 11/2011 | |
| WO | WO 2016/204217 A1 | 12/2016 | |
| WO | WO 2017/100782 A1 | 6/2017 | |
| WO | WO 2017/104558 A1 | 6/2017 | |
| WO | WO 2018/029970 A1 | 2/2018 | |

OTHER PUBLICATIONS

Zang et al. "Investigation on artificial blood vessels prepared from bacterial cellulose," Materials Science and Engineering C 46 (2015) 111-117. (Year: 2015).*
International Search Report (PCT/ISA/210) issued in PCT/JP2018/014895, dated Jul. 10, 2018.
Itoh et al., "Development of Small-Diameter Cell Artificial Blood Vessel Using Scaffold-Free Bio 3D Printer," Therapeutics & Engineering, vol. 29, No. 3, 2017, pp. 167-172.
Matsubayashi et al., "Development of Small Caliber Blood Vessels Modeled with Bio-3D Printer," The Medical Frontline, vol. 72, No. 12, Dec. 10, 2017, pp. 1686-1692.
Written Opinion of the International Searching Authority (PCT/ISA/237) issued in PCT/JP2018/014895, dated Jul. 10, 2018.
International Preliminary Report on Patentability and Written Opinion mailed Oct. 22, 2020, in PCT/JP2018/014895 (Forms (PCT/IB/326, PCT/IB/373, and PCT/ISA/237).
Extended European Search Report issued Mar. 16, 2021, in European Patent Application No. 18914693.9.

* cited by examiner

--PRIOR ART--

FIG. 4B

--PRIOR ART--

FIG. 4C

--PRIOR ART--

TUBULAR CELL STRUCTURE CULTIVATION MAINTAINING APPARATUS AND TUBULAR CELL STRUCTURE MAINTAINING SUPPORT DEVICE

TECHNICAL FIELD

The present invention relates to a maintaining apparatus and a maintaining support device for a tubular cell structure including a hollow portion inside.

BACKGROUND ART

Conventionally, as disclosed in PTL 1, a technique has been known that produces a three-dimensional structure by utilizing the characteristic that cell aggregates contacting each other in an adjacent manner are fused to each other, and three-dimensionally stacking the cell aggregates (spheroids) so that cell aggregates are adjacent to each other, by utilizing a support body formed by a plurality of needle-like bodies fixed in advance to extend in the normal direction of a substrate. Here, a cell aggregate refers to a lump of a plurality of cells formed by combining and cultivating single cells.

Figure 4A:
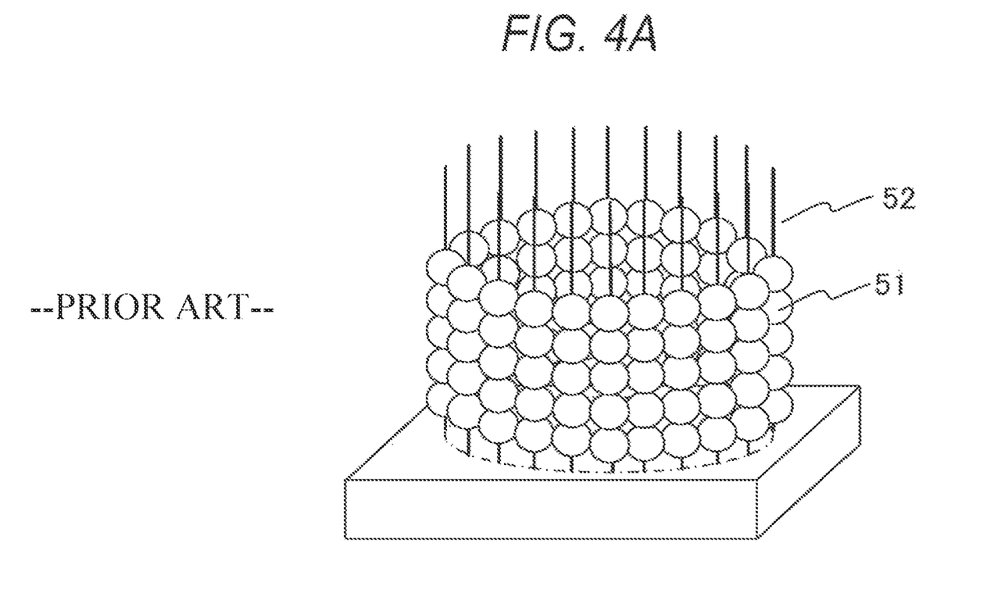
FIG. 4A is a schematic diagram illustrating the state where cell aggregates are stuck to needle-like bodies in the step of forming a cell structure.
Figure 4B:
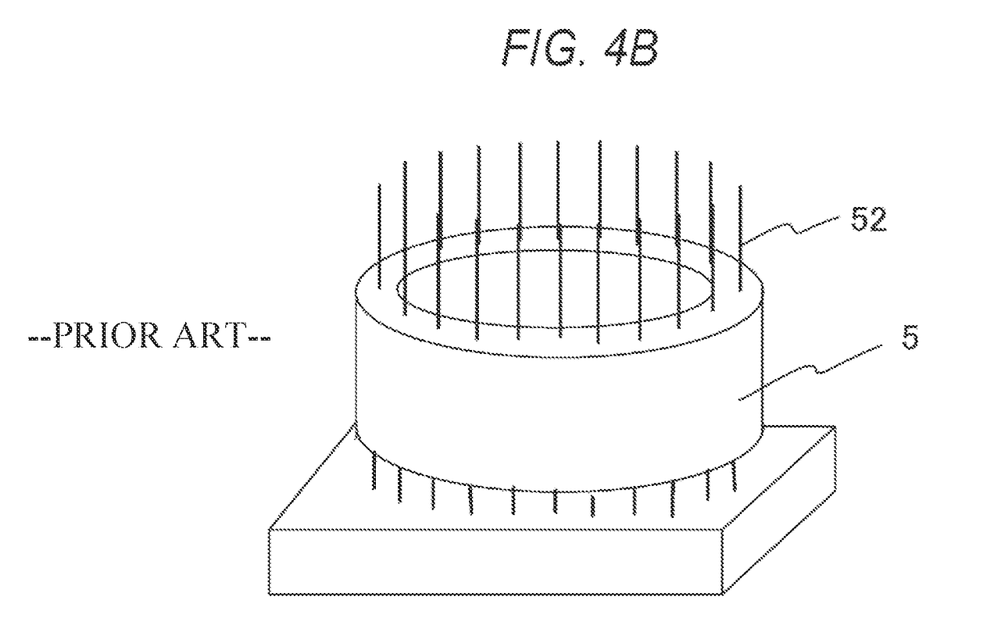
FIG. 4B is a schematic diagram illustrating the state where the adjacent cell aggregates are fused to each other to form the cell structure in the step of forming the cell structure.
Figure 4C:
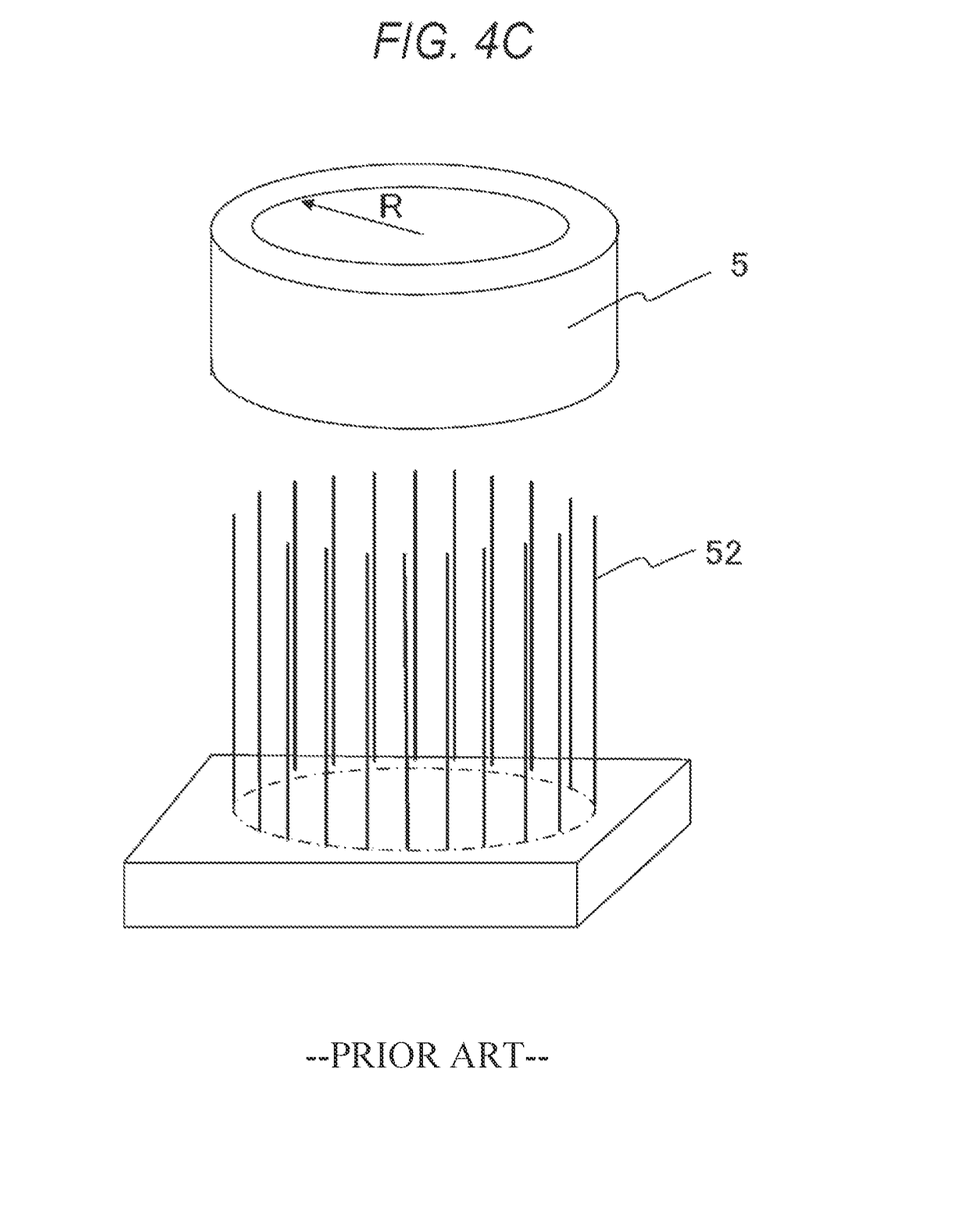
FIG. 4C is a schematic diagram illustrating the state showing the step of pulling out the formed cell structure from the needle-like bodies in the step of forming the cell structure.

In this technique, the technique is disclosed that extracts cell aggregates 51, and sticks each of the cell aggregates 51 to each of needle-like bodies of the support body to manufacture the state where the cell aggregates are skewered. For example, as in FIG. 4A, for example, as a cell structure 5 for blood vessel, needle-like bodies are arranged in a tubular shape, and the cell aggregates 51 are stuck to each of the needle-like bodies. When cultivated for a certain period of time, as shown in FIG. 4B, the adjacent cell aggregates 51 are fused to each other, and the tubular cell structure 5 is formed on the needle-like bodies 52. Then, as shown in FIG. 4C, when the cell structure 5 is pulled out from the needle-like bodies 52, the tubular cell structure 5 including a hollow portion inside the tube having a length L is extracted.

CITATION LIST

Patent Literature

PTL 1: Specification of Japanese Patent No. 4517125

SUMMARY OF INVENTION

Technical Problem

The cells constituting the cell structure 5 have the characteristic of fusing with adjacent cells.

Accordingly, when pulling out the tubular cell structure 5 from the needle-like bodies 52 to stand on its own, and preserving the cell structure 5 for only a predetermined period of time without each cell of the cell structure 5 destroyed, it is necessary to distribute a culture solution containing oxygen all over the outer surfaces and the inner surface of the cell structure 5. Additionally, further, in that case, there is a problem that, when opposing tubular walls contact each other, the cells in the contact portion are fused to each other, and a conduit is closed.

Solution to Problem

It is solved by a rod-shaped tubular cell structure maintaining support device for cultivating a tubular cell structure for a predetermined time period, the tubular cell structure including a hollow portion inside of the tubular cell structure, while maintaining the hollow portion, wherein the tubular cell structure maintaining support device includes an outer diameter insertable into the hollow portion of the cell structure, in a case where the rod-shaped tubular cell structure maintaining support device is inserted into the hollow portion, the outer diameter capable of allowing the tubular cell structure maintaining support device closely to contact an inner surface of the cell structure, and a penetration conduit including openings at both ends of the tubular cell structure maintaining support device, the penetration conduit penetrating between the openings, wherein the tubular cell structure maintaining support device has an oxygen permeable structure from the penetration conduit to an outer surface of the tubular cell structure maintaining support device.

It is solved by a tubular cell structure cultivation maintaining apparatus for cultivating a tubular cell structure for a predetermined time period, the tubular cell structure including a hollow portion inside the tubular cell structure, while maintaining the hollow portion, wherein the tubular cell structure cultivation maintaining apparatus including a culture chamber filled with a culture solution, the culture chamber including a first inlet and a second inlet for introducing the culture solution into the culture chamber, and a first exit and a second exit for discharging the culture solution from the culture chamber, a pump for circulating the culture solution, a first conduit that fluidly connects the first exit to the first inlet through the pump, a second conduit that fluidly connects the second exit to the second inlet through the pump, a rod-shaped member insertable into the hollow portion of the cell structure, the rod-shaped member including openings at both ends of the rod-shaped member, and a penetration conduit penetrating between the openings, and an adapter attachable to the second inlet, the adapter insertable into one of the openings of the penetration conduit to be fluidly connected to the second inlet, wherein the rod-shaped member has an oxygen permeable structure from the penetration conduit to an outer surface of the rod-shaped member, the rod-shaped member including an outer diameter capable of allowing the rod-shaped member closely to contact an inner surface of the cell structure in a case where the rod-shaped member is inserted into the hollow portion.

Advantageous Effects of Invention

According to the present invention, the hollow portion of the tubular cell structure can be maintained without being closed.

DESCRIPTION OF EMBODIMENTS

Figure 1:
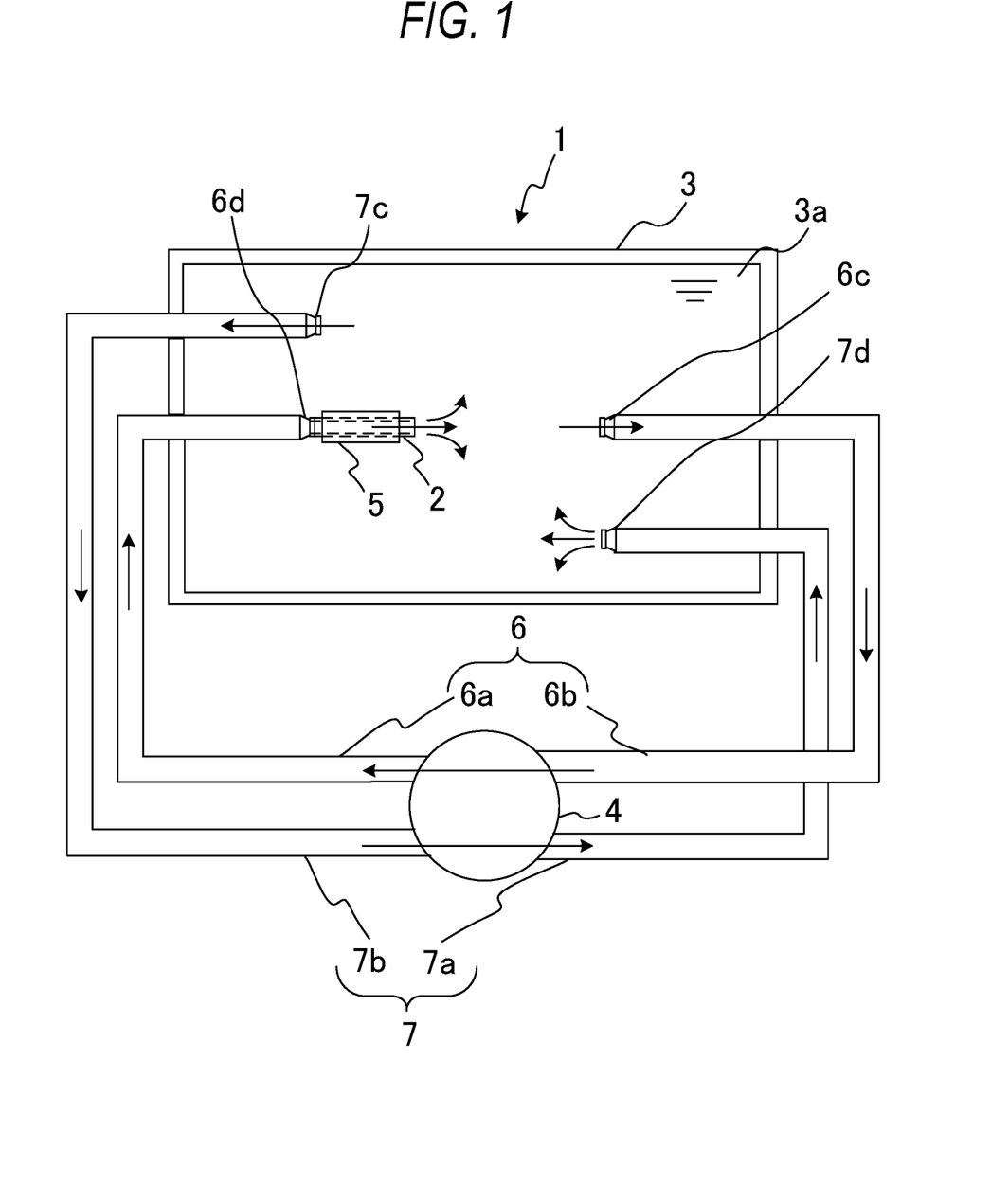
FIG. 1 is a diagram illustrating a tubular cell structure cultivation maintaining apparatus in the present invention.
Figure 2:
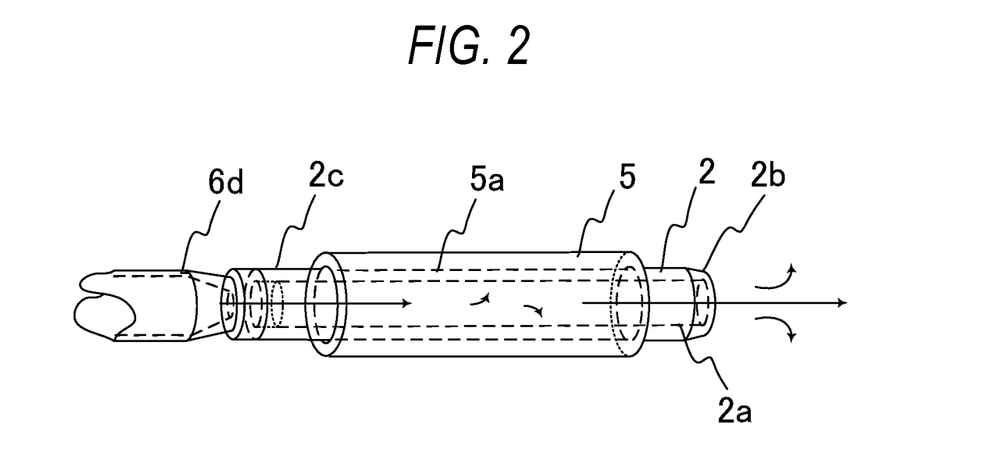
FIG. 2 is a diagram illustrating a tubular cell structure maintaining support device in the present invention, and illustrating the state where it is attached to the tubular cell structure cultivation maintaining apparatus.
Figure 3:
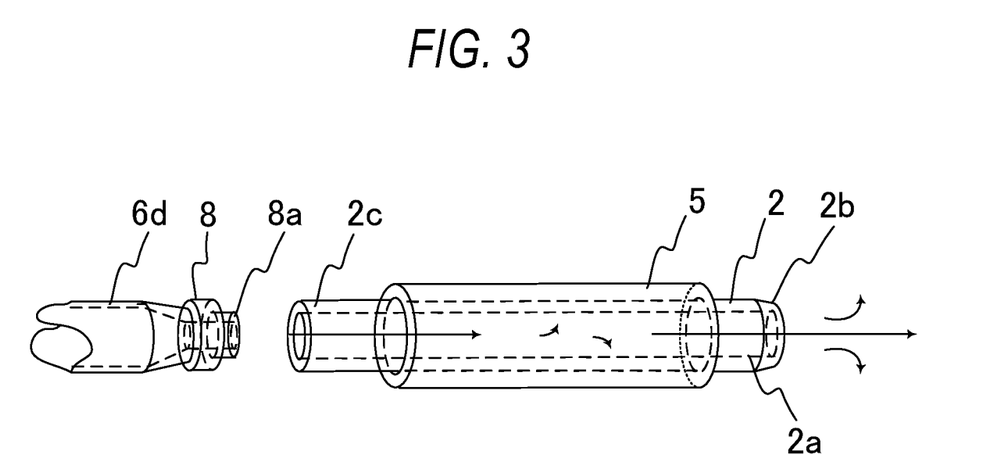
FIG. 3 is a diagram illustrating a tubular cell structure cultivation maintaining apparatus in the present invention, and illustrating the state where it is separated from the tubular cell structure cultivation maintaining apparatus.

First, referring to FIG. 1 to FIG. 3, a tubular cell structure cultivation maintaining apparatus 1 of the present invention will be described. FIG. 1 is a schematic diagram of the tubular cell structure cultivation maintaining apparatus 1 of an embodiment of the present invention. The tubular cell structure cultivation maintaining apparatus 1 includes a rod-shaped member 2 serving as a maintaining support device of the tubular cell structure 5, a culture chamber 3, a pump 4, a first conduit 6, a second conduit 7, and an adapter 8. FIG. 2 is a diagram illustrating the rod-shaped member 2, and illustrates a diagram of the state where it is attached to the tubular cell structure cultivation maintaining apparatus 1. Additionally, FIG. 3 is a diagram illustrating the rod-shaped member 2, and illustrates a diagram of the state where it has been detached from the tubular cell structure cultivation maintaining apparatus 1. The cell structure 5 was formed in, for example, the steps of FIG. 4A to FIG. 4C and the step as described above, and has a tubular structure including a hollow portion having a circular cross section inside the cell structure 5. In this specification, a description will be given by assuming that the radius of the hollow portion having the circular cross section of the cell structure 5 is R.

The culture chamber 3 is a sealed container, and the inside is filled with a culture solution 3a. The culture chamber 3 includes a first inlet 6d and a second inlet 7d for introducing the culture solution 3a into the culture chamber 3, and a first exit 6c and a second exit 7c for discharging the culture solution 3a from the culture chamber 3. The tubular cell structure cultivation maintaining apparatus 1 includes a first conduit 6 that fluidly connects the first exit 6c to the first inlet 6d through the pump 4, and a second conduit 7 that fluidly connects the second exit 7c to the second inlet 7d through the pump 4. The culture solution 3a is circulated inside the first conduit 6 and the second conduit 7 with the driving force of the pump 4. The first conduit 6 is mainly for supplying the culture solution 3a to the inside of the cell structure 5, and the second conduit 7 is mainly for spreading the culture solution 3a over the outside of the cell structure 5.

That is, when the culture chamber 3 filled with the culture solution 3a is seen as the starting point, the culture solution 3a flows out of the first exit 6c into a first conduit 6b, and travels toward the pump 4. Additionally, the culture solution 3a flows out of the second exit 7c into a second conduit 7b, and travels toward the pump 4. Thereafter, the culture solution 3a to which required nutrients and oxygen have been supplied at the pump 4 returns to the culture chamber 3 from the first conduit 6a through the first inlet 6d with the driving force of the pump 4. Additionally, it returns to the culture chamber 3 from the second conduit 7a through the second inlet 7d. The second inlet 7d, the first exit 6c, and the second exit 7c are open ends. The adapter 8 is attached to the first inlet 6d.

The rod-shaped member 2 is an elongated cylindrical member having a circular cross section. The outer diameter of the rod-shaped member 2 is R. At the stage of maintaining the cell structure 5, when the rod-shaped member 2 is inserted into the cell structure 5, the inner diameter of the cell structure 5 is slightly larger than the outer diameter R of the rod-shaped member 2. However, since the inner diameter of the cell structure 5 has the characteristic of gradually contracting in the course of maturation of cells that constitute the cell structure 5 with the elapse of time in the state where cultivation is being performed, the rod-shaped member 2 is tightly inserted and fit into the cell structure 5 without a gap between the cell structure 5 and the rod-shaped member 2. In the inside, a conduit 2a is provided so as to penetrate along the axial direction in the longitudinal direction of the rod-shaped member 2 from one end to the other end of the rod-shaped member 2. As for the length of the rod-shaped member 2, the rod-shaped member 2 is longer than at least the length of the cell structure 5. A top end 2b of the rod-shaped member 2 has a tapered shape so as to be easily inserted into the hollow portion of the cell structure 5.

The rod-shaped member 2 has a structure with oxygen permeability between the conduit 2a and the outer surface of the rod-shaped member 2. For example, small through-holes for oxygen penetration may be drilled between the conduit 2a of the rod-shaped member 2 of a fluoropolymer material and the outer surface of the rod-shaped member 2. Alternatively, an oxygen permeable material such as dimethylpolysiloxane (PDMS) may be used, without arranging the small through-holes for oxygen permeation. By introducing the oxygen-dissolved culture solution 3a into the conduit 2a, as the culture solution 3a passes, oxygen reaches the outer surface of the rod-shaped member 2, and the cell structure 5 can accept oxygen from the inner surface over the entire length of the cell structure 5.

A bottom end 2c, which is the opposite base of the rod-shaped member 2 to the top end 2b to which the taper is arranged, has a structure that can be fit to the adapter 8. Since a fitting port 8a of the adapter 8 can be easily inserted and fit into the conduit 2a in the bottom end 2c of the rod-shaped member 2, one-touch insertion can be performed. For example, as in FIG. 2, the rod-shaped member 2 can be attached to the first inlet 6d through the adapter 8, and as shown in FIG. 3, the rod-shaped member 2 can be easily detached from the first inlet 6d through the adapter 8.

Subsequently, how to use the tubular cell structure cultivation maintaining apparatus 1 and the rod-shaped member 2 serving as the tubular cell structure maintaining support device will be described. First, the tubular cell structure 5 is formed, based on the method described in the background art. Then, the rod-shaped member 2 is inserted into the hollow portion of the tubular cell structure 5, so as to cause the inner surface of the cell structure 5 to adhere to the outer periphery surface of the rod-shaped member 2. In this state, in the state where the rod-shaped member 2 has been inserted into the hollow portion of the cell structure 5, the rod-shaped member 2 is attached to the first inlet 6d through the adapter 8 and installed in the tubular cell structure cultivation maintaining apparatus 1, and with the tubular cell structure cultivation maintaining apparatus 1, the culture solution 3a allowing permeation of oxygen is passed through the inside of the conduit 2a of the rod-shaped member 2, and the inside and outside of the cell structure 5 are immersed in the culture solution 3a, and cultured and matured for a predetermined period of time. The sufficient culture solution 3a is supplied to the cell structure 5 during the period of time.

REFERENCE SIGNS LIST 1 tubular cell structure cultivation maintaining apparatus, 2 rod-shaped member, 2a conduit, 2b top end, 2c bottom end, 3 culture chamber, 3a culture solution, 4 pump, 5 cell structure, 6 first conduit, 7 second conduit, 8 adapter, 8a fitting port

The invention claimed is:

1. A rod-shaped tubular cell structure maintaining support device for cultivating a preformed tubular cell structure for a predetermined time period, the preformed tubular cell structure having a hollow portion inside of the tubular cell structure, wherein opposing tubular inside-walls of the preformed tubular cell structure tend to contact each other and be fused to each other so that the hollow portion of the preformed tubular cell structure is closed during the predetermined time period, wherein the rod-shaped tubular cell structure maintaining support device comprises:

an outer diameter wherein when the rod-shaped tubular cell structure maintaining support device is inserted into the preformed tubular cell structure, the outer diameter of the rod-shaped tubular cell structure maintaining support device is slightly smaller than the inner diameter of the preformed tubular cell structure, and according to the elapse of time when cultivation is being performed in the predetermined time period, the rod-shaped tubular cell structure maintaining support device is tightly inserted and fit into the cell structure without a gap between the preformed tubular cell structure and the rod-shaped tubular cell structure maintaining support device; and a penetration conduit including openings at both ends of the tubular cell structure maintaining support device, the penetration conduit configured to flow a culture solution not including cells, the penetration conduit penetrating between the openings, wherein the rod-shaped tubular cell structure maintaining support device has an oxygen permeable structure from the penetration conduit to an outer surface of the tubular cell structure maintaining support device, wherein the rod-shaped tubular cell structure maintaining support device is constructed so as to maintain the tubular open structure of said tubular cell structure when said rod-shaped tubular cell structure maintaining support device is detached from a cultivation maintaining apparatus, and wherein the oxygen permeable structure is:

dimethylpolysiloxane as a material of the tubular cell structure maintaining support device to enhance an oxygen permeability.

2. A tubular cell structure cultivation maintaining apparatus for cultivating a preformed tubular cell structure for a predetermined time period, the preformed tubular cell structure having a hollow portion inside the tubular cell structure wherein opposing tubular inside-walls of the preformed tubular cell structure tend to contact each other and be fused to each other so that the hollow portion of the preformed tubular cell structure is closed during the predetermined time period, wherein the tubular cell structure cultivation maintaining apparatus comprises:

a culture chamber filled with a culture solution, the culture chamber including a first inlet and a second inlet for introducing the culture solution into the culture chamber, and a first exit and a second exit for discharging the culture solution from the culture chamber;

a pump for circulating the culture solution;

a first conduit that fluidly connects the first exit to the first inlet through the pump;

a second conduit that fluidly connects the second exit to the second inlet through the pump;

a rod-shaped member having enough strength to maintain the shape of the hollow portion of the tubular cell structure can be maintained without being closed, and said rod-shaped member being configured to be inserted into the hollow portion of the preformed tubular cell structure, the rod-shaped member including an outer diameter wherein when the rod-shaped member is inserted into the preformed tubular cell structure, the outer diameter of the rod-shaped member is slightly smaller than the inner diameter of the preformed tubular cell structure, and according to the elapse of time when cultivation is being performed in the predetermined time period, the rod-shaped member is tightly inserted and fit into the cell structure without a gap between the preformed tubular cell structure and the rod-shaped member, openings at both ends of the rod-shaped member, a penetration conduit penetrating between the openings, and the penetration conduit configured to flow a culture solution not including cells, wherein the rod-shaped member is constructed so as to maintain the tubular open structure of said tubular cell structure when said rod-shaped member is detached from the cultivation maintaining apparatus; and an adapter attachable to the second inlet, the adapter insertable into one of the openings of the penetration conduit to be fluidly connected to the second inlet, wherein the rod-shaped member has an oxygen permeable structure from the penetration conduit to an outer surface of the rod-shaped member, wherein the oxygen permeable structure is:

dimethylpolysiloxane as a material of the tubular cell structure maintaining support device to enhance an oxygen permeability.

3. A rod-shaped tubular cell structure maintaining support device for cultivating a preformed tubular cell structure for a predetermined cultivation time period, the preformed tubular cell structure having a hollow portion inside of the tubular cell structure, wherein opposing tubular inside-walls of the preformed tubular cell structure tend to contact each other and be fused to each other so that during the predetermined time period the hollow portion of the preformed tubular cell structure becomes closed, comprising:

a rod-shaped tubular cell structure maintaining support device capable of being inserted into the hollow portion of the preformed tubular cell structure and having enough strength to prevent the hollow portion of the tubular cell structure from closing, said rod-shaped tubular cell structure maintaining support device comprising:

an outer diameter with a first end that is tapered whereby the rod-shaped tubular cell structure maintaining support device is capable of being inserted into the preformed tubular cell structure, said outer diameter of said rod-shaped tubular cell structure maintaining support device being slightly smaller than the inner diameter of the preformed tubular cell structure, and during said predetermined cultivation time period, the rod-shaped tubular cell structure maintaining support device becomes tightly fitted into the cell structure without a gap between the preformed tubular cell structure and the rod-shaped tubular cell structure maintaining support device; and a penetration conduit including openings at both ends of the tubular cell structure maintaining support device, the penetration conduit configured to flow a culture solution not including cells, wherein the rod-shaped tubular cell structure maintaining support device has an oxygen permeable structure from the penetration conduit to an outer surface of the tubular cell structure maintaining support device, and wherein the rod-shaped tubular cell structure maintaining support device is constructed so as to maintain the tubular open structure of said tubular cell structure when said rod-shaped tubular cell structure maintaining support device is detached from a cultivation maintaining apparatus.

4. A rod-shaped tubular cell structure maintaining support device for cultivating a preformed tubular cell structure for a predetermined cultivation time period while maintaining a hollow portion inside of the preformed tubular cell structure, the rod-shaped tubular cell structure maintaining support device comprising:
(a) an outer diameter that is slightly smaller than the inner diameter of the hollow portion of the preformed tubular cell structure, whereby the rod-shaped tubular cell structure maintaining support device is capable of being tightly inserted and fit into the hollow portion without a gap between the rod-shaped tubular cell structure maintaining support device and the hollow portion of the preformed tubular cell structure;
(b) a penetration conduit including openings at both ends of the tubular cell structure maintaining support device, the penetration conduit configured to flow a culture solution not including cells,
(c) an oxygen permeable structure from the penetration conduit to an outer surface of the tubular cell structure maintaining support device,
(d) a first end that is tapered to permit insertion into the hollow portion of the preformed tubular structure; and
(e) a second end including an adapter capable of being easily connected to a source of a flow of an oxygenated cell culture solution, wherein
the rod-shaped tubular cell structure maintaining support device has enough strength to prevent the hollow portion of the tubular cell structure from closing.

5. A tubular cell structure cultivation maintaining apparatus for cultivating a preformed tubular cell structure for a predetermined time period, the preformed tubular cell structure having a hollow portion inside the tubular cell structure wherein opposing tubular inside-walls of the preformed tubular cell structure tend to contact each other and be fused to each other and be fused to each other so that during the predetermined time period the hollow portion of the preformed tubular cell structure becomes closed, wherein the tubular cell structure cultivation maintaining apparatus comprising:
a culture chamber filled with a culture solution, the culture chamber including a first inlet and a second inlet for introducing the culture solution into the culture chamber, and a first exit and a second exit for discharging the culture solution from the culture chamber;
a pump for circulating the culture solution;
a first conduit that fluidly connects the first exit to the first inlet through the pump;
a second conduit that fluidly connects the second exit to the second inlet through the pump; and
a rod-shaped tubular cell structure maintaining support device capable of being inserted into the hollow portion of the preformed tubular cell structure and having enough strength to prevent the hollow portion of the tubular cell structure from closing, comprising:
an outer diameter with a first end that is tapered whereby the rod-shaped tubular cell structure maintaining support device is capable of being inserted into the preformed tubular cell structure, said outer diameter of said rod-shaped tubular cell structure maintaining support device being slightly smaller than the inner diameter of the preformed tubular cell structure, and during said predetermined cultivation time period, the rod-shaped tubular cell structure maintaining support device becomes tightly fitted into the cell structure without a gap between the preformed tubular cell structure and the rod-shaped tubular cell structure maintaining support device; and
a penetration conduit including openings at both ends of the tubular cell structure maintaining support device, the penetration conduit configured to flow a culture solution not including cells,
wherein the rod-shaped tubular cell structure maintaining support device has an oxygen permeable structure from the penetration conduit to an outer surface of the tubular cell structure maintaining support device.

6. A tubular cell structure cultivation maintaining apparatus for cultivating a preformed tubular cell structure for a predetermined time period, the preformed tubular cell structure having a hollow portion inside the tubular cell structure wherein opposing tubular inside-walls of the preformed tubular cell structure tend to contact each other and be fused to each other and be fused to each other so that during the predetermined time period the hollow portion of the preformed tubular cell structure becomes closed, wherein the tubular cell structure cultivation maintaining apparatus comprising:
a culture chamber filled with a culture solution, the culture chamber including a first inlet and a second inlet for introducing the culture solution into the culture chamber, and a first exit and a second exit for discharging the culture solution from the culture chamber;
a pump for circulating the culture solution;
a first conduit that fluidly connects the first exit to the first inlet through the pump;
a second conduit that fluidly connects the second exit to the second inlet through the pump; and
a rod-shaped tubular cell structure maintaining support device for cultivating a preformed tubular cell structure for a predetermined cultivation time period while maintaining a hollow portion inside of the preformed tubular cell structure, the rod-shaped tubular cell structure maintaining support device comprising:
(a) an outer diameter that is slightly smaller than the inner diameter of the hollow portion of the preformed tubular cell structure, whereby the rod-shaped tubular cell structure maintaining support device is capable of being tightly inserted and fit into the hollow portion without a gap between the rod-shaped tubular cell structure maintaining support device and the hollow portion of the preformed tubular cell structure;
(b) a penetration conduit including openings at both ends of the tubular cell structure maintaining support device, the penetration conduit configured to flow a culture solution not including cells,
(c) an oxygen permeable structure from the penetration conduit to an outer surface of the tubular cell structure maintaining support device,
(d) a first end that is tapered to permit insertion into the hollow portion of the preformed tubular structure; and (e) a second end including an adapter capable of being easily connected to a source of a flow of an oxygenated cell culture solution, wherein the rod-shaped tubular cell structure maintaining support device has enough strength to prevent the hollow portion of the tubular cell structure from closing.

\* \* \* \* \*